United States Patent [19]

Campbell

[11] Patent Number: 4,903,690

[45] Date of Patent: Feb. 27, 1990

[54] SPINAL ORTHOTIC DEVICE AND METHOD OF USING SAME

[76] Inventor: Clayton J. Campbell, 17181 Eastview Dr., Chagrin Falls, Ohio 44022

[21] Appl. No.: 244,091

[22] Filed: Sep. 14, 1988

[51] Int. Cl.$^4$ ................................................ A61F 5/01
[52] U.S. Cl. .......................................... 128/78; 5/434; 128/68; 128/898; 264/45.2; 264/222; 264/314
[58] Field of Search ...................... 128/898, 70, 78, 68; 5/434, 481, 450, 436; 297/460, DIG. 1, DIG. 2; 264/222, DIG. 30, 45.2, 314

[56] References Cited

U.S. PATENT DOCUMENTS

| | | | |
|---|---|---|---|
| 2,727,278 | 12/1955 | Thompson | 297/DIG. 1 |
| 3,830,896 | 8/1974 | Flicker et al. | 5/450 |
| 4,114,214 | 9/1978 | Von Heck | 5/450 |
| 4,347,213 | 8/1982 | Rogers, Jr. | 264/222 |
| 4,615,856 | 10/1986 | Silverman | 264/222 |
| 4,622,185 | 11/1986 | Kostich | 264/222 |
| 4,710,991 | 12/1987 | Wilmore et al. | 128/68 |

FOREIGN PATENT DOCUMENTS

| | | | |
|---|---|---|---|
| 2250681 | 4/1974 | Fed. Rep. of Germany | 264/222 |
| 3145770 | 5/1983 | Fed. Rep. of Germany | 264/222 |

OTHER PUBLICATIONS

Bender, *Handbook of Foamed Plastics*, Lake Pub, Libertyville, Ill., pp. 10, 11, 222.

Primary Examiner—Edgar S. Burr
Assistant Examiner—Moshe I. Cohen
Attorney, Agent, or Firm—James H. Tilberry

[57] ABSTRACT

A customized spinal orthotic device is provided to enhance spinal adjustment and manipulative procedures. The embodiment of the orthotic device shown and described is a plastic head and cervical basin which is enclosed in a plastic bag. The patient is placed in a supine position with the head and cervical spine portion received within the plastic basin but exterior of the bag. Commercial flexible polyurethane foam A and B components are mixed and placed in the bag-enclosed basin. The A and B components react exothermically to expand and to apply pressure to the cervical spine portion contained within the basin. In about fifteen minutes the polyurethane hardens to form a foam mold for the posterior apophyseal joints of the cervical spine and in the process urges the joints of the spine into their normally aligned positions. The mold may then be used by the patient on a daily basis within the purview of a clinical care program to enhance the effect of the spinal adjustment and/or manipulative procedure. Other shaped basins and trays may be designed for similar treatment of other regions of the spine using the same method of treatment.

2 Claims, 4 Drawing Sheets

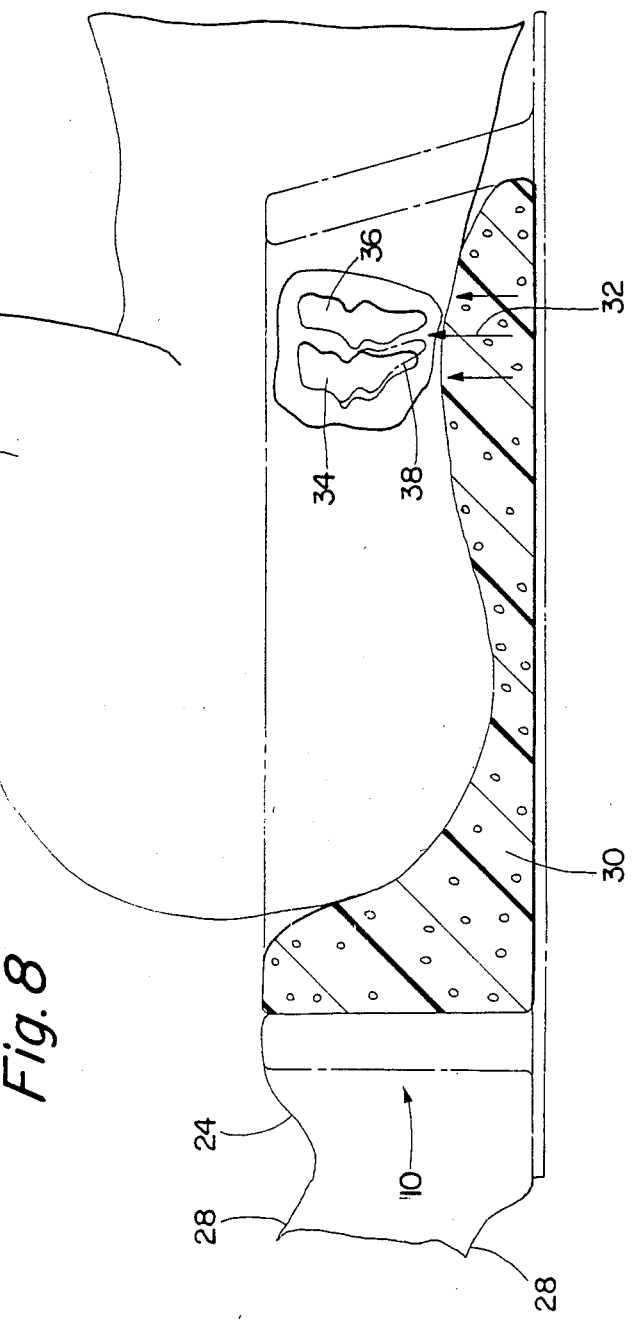

SPINAL ORTHOTIC DEVICE AND METHOD OF USING SAME

This invention relates in general to articular neurology and manipulative therapy. In particular, the invention relates to the Vertebral Subluxation Complex (VSC) as it concerns a group of spinal joint dysfunctions with neurophysiological consequences.

All synovial joints of the body including the apophyseal joints of the vertebral column are provided with four varieties of receptor nerve endings. These nerve endings are identified as Types I, II, III and IV by B. D. Wyke in his article entitled "Articular Neurology and Manipulative Therapy," published by Lincoln Institute of Health Sciences, Carlton, Victoria, Australia, in *Aspects of Manipulative Therapy*. The subject invention is adapted to treat Type II and Type III receptors, which are encapsulated corpuscular mechanoreceptors (i.e. biological transducers) that are stimulated by increases in tension in the tissue in which they are embedded. The Type II mechanoreceptors are embedded in the deeper layers of the fibrous capsule. The Type III mechanoreceptors are larger than Type II receptors, and are thinly encapsulated corpuscles that are applied to the surfaces of joint ligaments. This invention is concerned with the intrinsic muscles of the spine which are controlled by Type II and Type III mechanoreceptors. Type III receptors differ from Type II receptors in that Type III receptors respond to applied external forces, whereas Type II receptors respond to lower consistent forces.

It is among the objects of this invention to provide an orthotic device which, when used in accordance with the teaching of this invention, reduces vertebral subluxation; enhances joint motion toward a more normal function; and assists in spinal adjustment and manipulative procedures.

The foregoing and other objects, features, and advantages of the invention will become apparent from the description set forth hereinafter when considered in conjunction with the accompanying drawings, wherein:

FIG. 8 is an enlarged schematic elevational view, partially in section, showing in greater detail a patient's cervical spine being acted upon by an expanding polymer foam.

In the prior art of manipulative therapy, it is established procedure to treat Vertebral Subluxation Complex (VSC) by adjustments of the spinal vertebrae. By applied hand pressure, the therapist is able to correct the dysfunction. Since spinal misalignments are oftentimes of an order of approximately 0.001 mm., a slight pressure, properly applied, will suffice to accomplish realignment. Reference is made to "The Vertebral Subluxation Complex Research Insights," published by Renaissance International, S. A. and "Neuro-physiological Research on the Consequences of Joint Fixation," Department of Psychology, University of Colorado, Boulder, Colorado, Dec. 3, 1977. This method of hand manipulation of the vertebrae may be referred to as the acute care method of practice, by which relief is obtained by addressing the symptom. Although the relief may be instantaneous, and, to the patient, may seem miraculous, the manipulation is not a cure, and it is not unusual for the dysfunction to recur. The reason for this spinal recidivism is that the tissues associated with the misaligned vertebrae were most likely initially injured in some manner, thereby contributing to the misalignment. To merely realign the vertebrae does not contribute to or otherwise enhance tissue healing sufficiently to hold the vertebrae permanently in place. Thus, the spinal condition of the patient becomes chronic, requiring repeated visits to the therapist for additional manipulations.

Only within the past several years has a new concept of patient care developed called the reconstructive care method. With this new method, the object is to bring about permanent structural change in the spine, thereby providing the patient with permanent, rather than temporary, relief.

The subject invention is a device and method for practicing reconstructive care.

Figure 1:
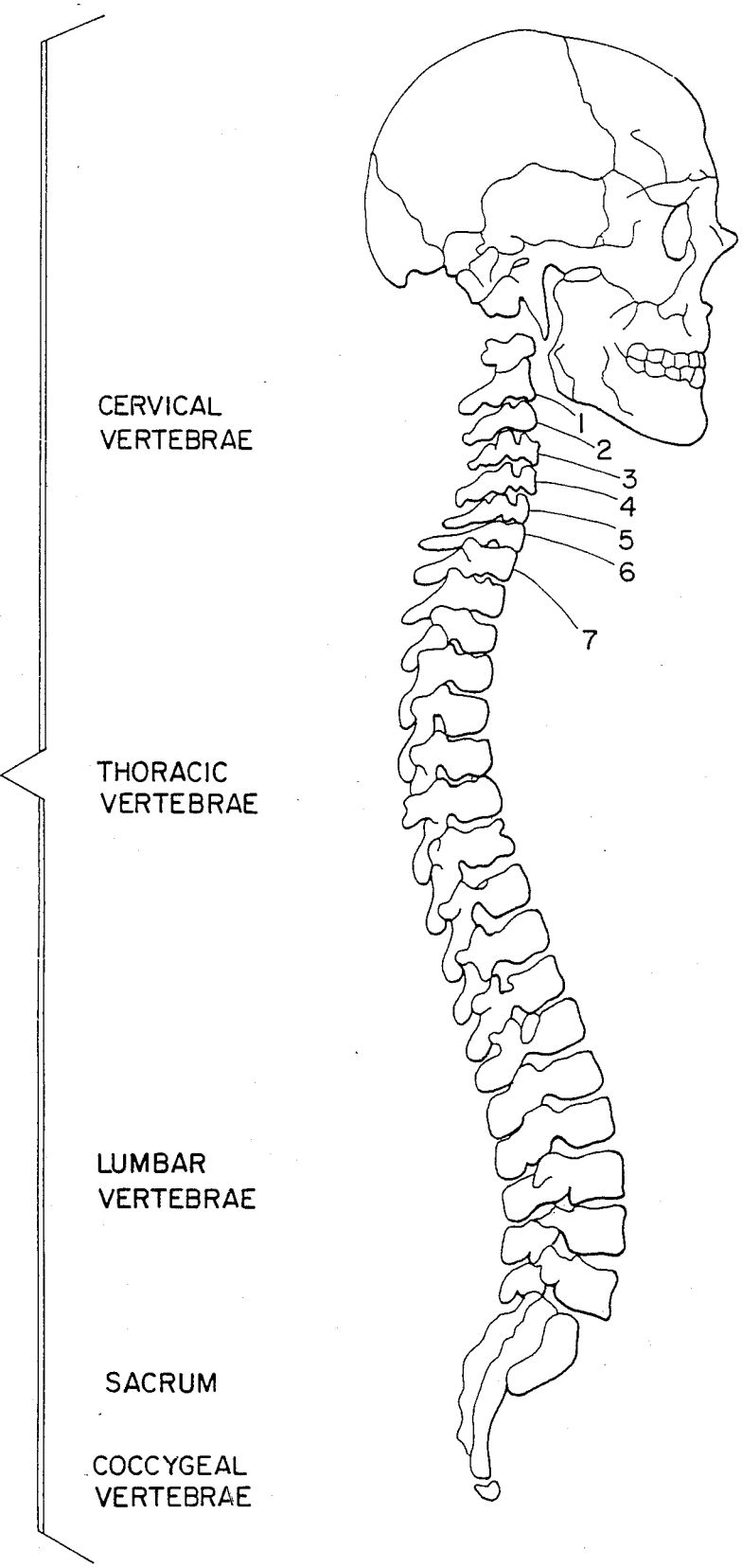
FIG. 1 is an elevational schematic sketch of a human skull and the vertebrae connected thereto.
Figure 2:
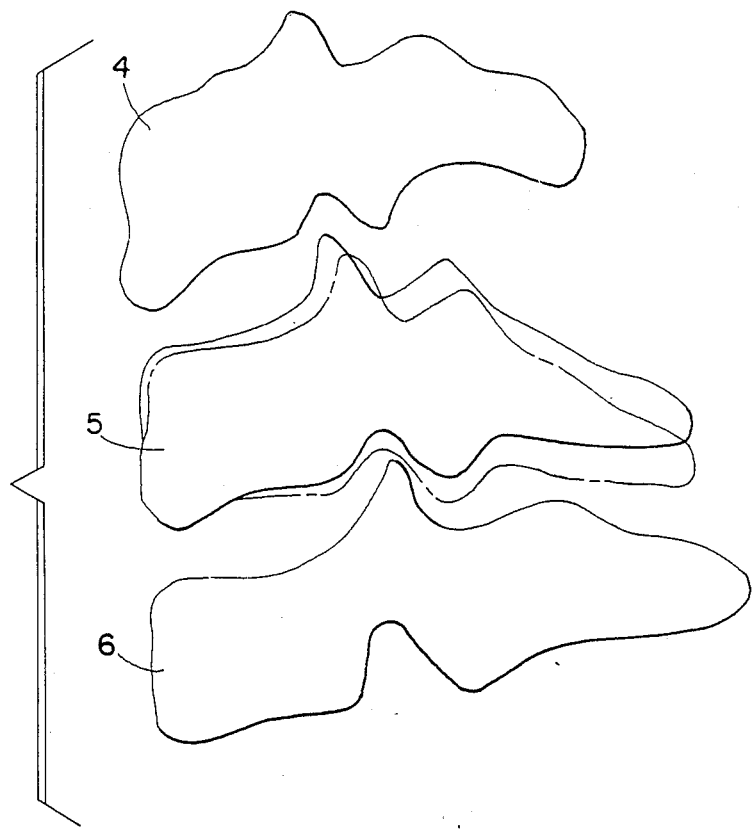
FIG. 2 is an enlarged schematic elevational sketch of the fourth, fifth, and sixth vertebrae, showing a dysfunction of the fifth vertebra in phantom.

Referring now to FIG. 1, therein is disclosed a schematic sketch of a normal spinal column, showing the first seven spinal vertebrae indicated by the numerals 1–7. It will be noted that the vertebrae are substantially equally spaced apart. However, FIG. 2 shows a dysfunction of vertebra No. 5 in phantom, wherein vertebra No. 5 is closer to vertebra No. 6 than to vertebra No. 4.

Figure 3:
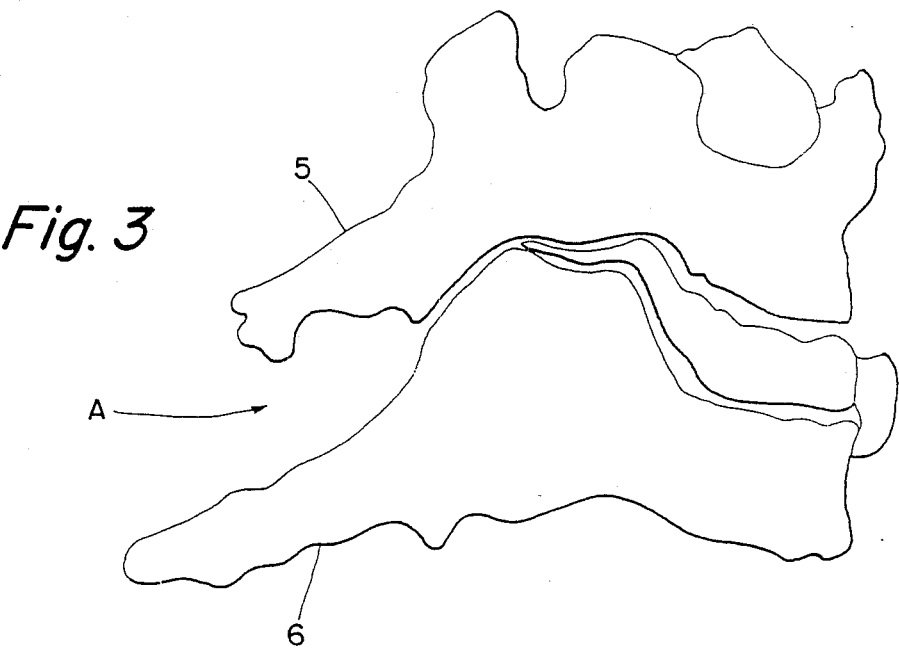
FIG. 3 is an enlarged schematic elevational sketch of a motor unit comprising a pair of vertebrae and all soft tissue components associated therewith.

FIG. 3 is another view of vertebrae 5 and 6 comprising a motor unit, which is defined as a functional unit of the spine, including two vertebrae, a disc, and all muscles, ligaments, and other constituents of tissue. The recognized treatment for the dysfunction shown in FIG. 2 is to apply pressure in the direction of the arrow A of FIG. 3 against the soft tissue components of the motor unit to shift vertebra No. 5 back into proper alignment.

The Applicant is an advocate of the reconstructive care method of practice, and has carefully followed and applied the advances made in this relatively new field while also looking for and thinking about new solutions to problems presented by the requirements of reconstructive care. Eventually, Applicant decided to investigate the possibility of developing an orthopedic device which could be applied to any segment of the spine to assist in the restoration or improvement of its function. He concluded that such a device would have to meet the following four tests:

1. It should be customized to the patient to provide consistent repeatable results.
2. It should have the ability to enhance the effect of spinal adjustments.
3. It should be easy to use by the patient and should not interfere with the patient's lifestyle.
4. It should not only have the patient's acceptance, but also the patient must actually like the device, and want to use it.

It was Applicant's belief that if a customized spinal orthotic device could be utilized by the patient at home, this would enhance the spinal adjustment, encourage healing of the motor tissue, and assist the patient to offset daily environmental stresses related to VSC. A search of the literature on spinal orthosis has revealed a scarcity of work in this area, the patent to Max Lerman, No. 4,628,913 being representative of the types of orthotic devices presently available. This patent, captioned "Cervical Thoracic Orthosis," is nothing more than a harness for immobilizing the head and neck region of a patient.

Quite by chance, Applicant observed that a device with which he was experimenting to act as a head restraint for the purpose of taking X-rays seemed to cause a favorable adjustment of a dysfunction for which the patient was being treated. Further observation encouraged Applicant to undertake a controlled study in which patients were chosen from four chiropractic clinics. The patients chosen were difficult cases whose chiropractic care had plateaued.

The method used to treat these patients comprised the following steps and procedures:
1. Each subject was placed in the supine position on an examination table.
2. A plastic bag-covered basin was then placed under the subject's cervical spine for positioning.
3. The patient was then elevated momentarily while a two-part polyurethane flexible foam chemical formula was mixed.
4. The resulting mixture was then poured into the basin in the area approximated by the mid-cervical spine.
5. The patient was then returned to the supine position with his head resting in the basin.
6. The polyurethane mixture would then begin to expand and harden in exothermic reaction, a process which takes approximately fifteen minutes.
7. The hardened foam formed a rigid impression of the posterior cervical spinal section.
8. While expanding, the foam applied corrective pressure against the spinal dysfunction.

The patient was instructed to utilize the form thereafter by resting his head in it for fifteen minutes at the end of each day for a period of eight weeks, and his doctors were instructed simply to see the subject on their regular program of care.

Doctors of varying technique preference were chosen in order to minimize the effect of technique upon the final result. Statistics were kept regarding the need for additional spinal adjustments. The patients' histories were then compared to their histories compiled during an eight-week period prior to the study, and the results were analyzed by a statistician. Improvements were noted as follows:
1. For the cervical vertebrae, the average improvement in number of adjustments needed was 60%.
2. For the thoracic vertebrae, the average improvement in number of adjustments needed was 54%.
3. In at least one instance, analysis clearly indicated that the orthosis had produced an improvement in the dysfunction which was indistinguishable from manipulative adjustment.
4. In one instance, the patient experienced abatement of tinnitus.
5. In another instance, the patient discovered that by using the orthosis for forty-five minutes during an episode of cephalgia (migraine), complete abatement of the symptom was obtained.

The following description of a preferred embodiment of the invention relates to an orthotic device for treatment of the cervical vertebrae region of the spine. However, the principle is the same and the same teaching may also be applied to treatment of the other portions of the spine, i.e. the thoracic, lumbar, sacrum and coccygeal spinal regions. It is to be understood, therefore, that the specific orthotic device described herein and shown in the drawings is for purposes of illustration only.

Figure 4:
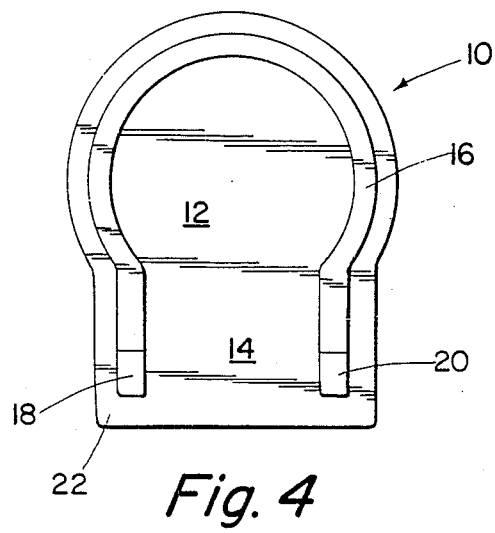
FIG. 4 is a plan view of a plastic basin used in the practice of the invention.
Figure 5:
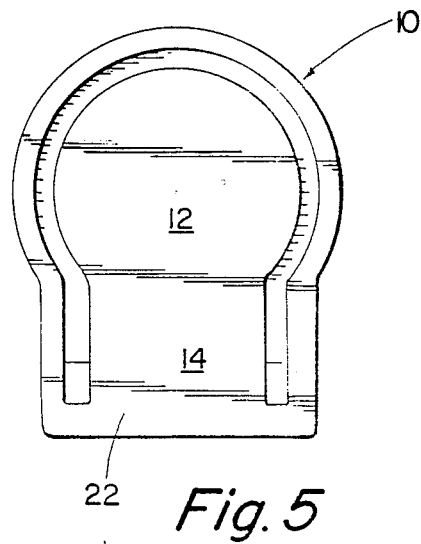
FIG. 5 is a bottom view of the basin shown in FIG. 4.
Figure 6:
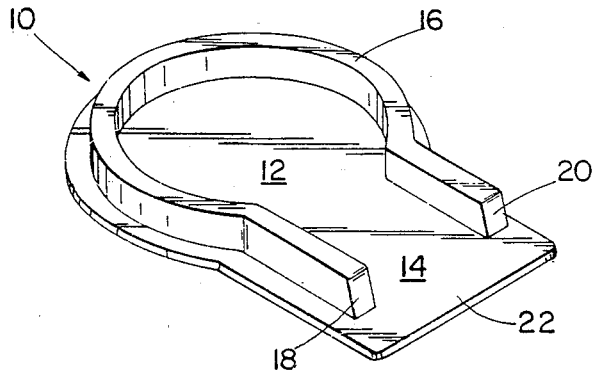
FIG. 6 is a perspective view of the basin shown in FIG. 4.

Referring now to FIGS. 4, 5 and 6, therein is shown the basin 10 developed by Applicant to practice his procedure for treatment of the cervical vertebrae. The basin is a thin, lightweight blow molded orthosis providing head area 12, a neck or cervical area 14, and a retaining dam 16. The head area is approximately 9" in diameter, and the neck area is approximately 7" between dam ends 18 and 20. The dam is hollow, approximately 1" thick, and extends approximately 3" above the basin base 22.

Figure 7:
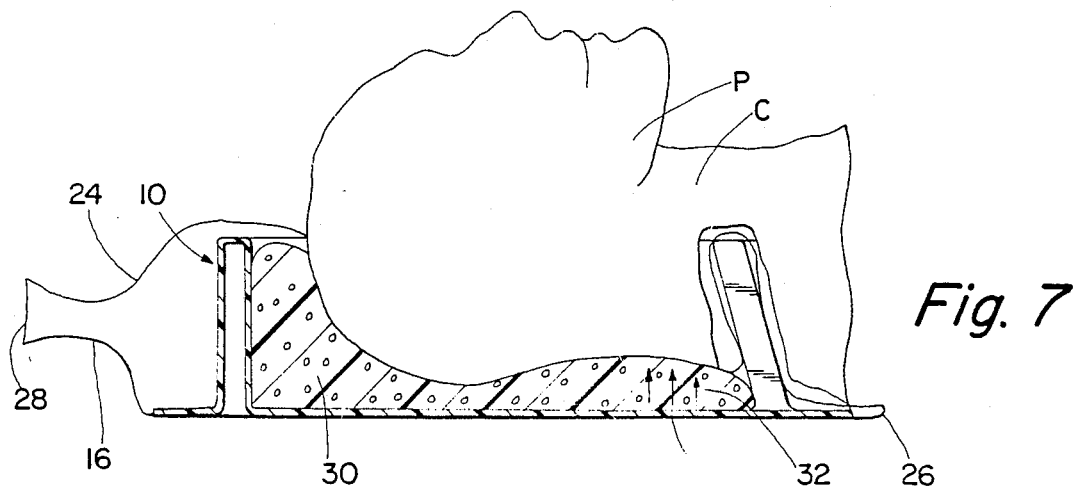
FIG. 7 is a schematic elevational view, shown partially in section, showing a patient's cervical spine being acted upon by an expanding polymer foam.

Referring now to FIG. 7, therein is shown the basin 10 encased in a plain household vinyl bag 24, having a closed end 26 and an open end 28. As already discussed, a mixture of exothermic reacting polyurethane foam components 30 is placed in the basin 10 in the cervical area 14 so as to assure expansion on the underside of the cervical vertebrae C of the patient P and the application of upward pressure against the cervical vertebrae C, as shown by the arrows 32. Sufficient polyurethane mix is placed in the basin to also permit expansion throughout, so that a contoured head rest is provided for the patient. Properly measured, the polyurethane expansion will fill, but not overflow, the basin. Similar basins or trays may be designed and particularly adapted, as required, for the treatment of the other regions of the spine.

Referring to FIG. 8, therein is schematically shown the vertebrae of a motor unit comprising a pair of vertebrae in which there is initially a dysfunction of vertebra 34 relative to vertebra 36, as shown in phantom at 38. The pressure of the expanding polyurethane foam 30, as shown by arrows 32, applies pressure between vertebrae 34 and 36, whereby vertebra 34 is adjusted to the position shown in solid lines. The expanding polyurethane additionally provides vectors of force to all other joints within the orthosis.

The Type III mechanoreceptors, embedded in the joint ligaments of the spinal segments, are sensitive to stretch such as results from the expanding polyurethane foam pressure. Once stretched, they cause an alteration in the contraction of the intrinsic muscles of the spine. The intrinsic muscles of the spine are primarily designed to deal with the individual motor units of the spine, which include, as aforesaid, two vertebrae, a disc, and all muscles, ligaments, and other tissue constituents. The mechanoreceptor stretch reflex, therefore, normalizes the intrinsic muscle function, which, in turn, causes a reduction in hypertonic muscles. There follows a reduction of the displaced fixated joint site. The foam mold serves as a template for the subluxated joints. Thus, the subsequent regular and periodic placement of subluxated joint sites on the template will cause stretch reflex to activate and cause the same beneficial reflex response of Type II mechanoreceptors.

After about fifteen minutes the polyurethane foam will solidify. The patient then takes the mold home, and each day assumes the supine position with the head and underside of the cervical spine supported by the foam mold. This procedure corrects minor dysfunctions on a daily basis, thereby permitting the motor tissues to heal, gain strength, and hold the chronically dysfunctional vertebrae in place. Although the results of this procedure vary from patient to patient, on an average, good results are noticed after about eight weeks of treatment with the orthotic device.

Applicant is unaware of any appreciation whatsoever by those skilled in the art that a static orthotic device could be used to obtain therapeutic benefits heretofore believed only possible by spinal manipulation and adjustment. Applicant's orthotic device and method do not eliminate the need for spinal treatment, but is, instead, another valuable tool and procedure now available to practitioners of manipulative therapy.

It will occur to those skilled in the art, having read the described preferred embodiments of the invention and having read the specification in conjunction with a study of the drawings, that certain modifications may be made to the invention. However, it is intended that the invention only be limited by the scope of the appended claims.

What is claimed is:

1. The method of treating vertebral subluxation complex of the human spine comprising the steps of:
    (a) providing permanent lightweight one-piece containment means for the region of the spine to be treated;
    (b) freely positioning the region of the spine to be treated within the confines of said containment means without restraint;
    (c) interposing a pliable membrane means between said containment means and said region of the spine to be treated;
    (d) placing an exothermic reacting expanding polymer foam in said containment means in the area approximated by the region of the spine to be treated;
    (e) permitting said polymer foam to expand between said containment means and said membrane and to apply corrective pressure to said region of the spine to be treated;
    (f) permitting said polymer foam to form an impression of said region of the spine to be treated without permitting said polymer foam to immobilize the patient;
    (g) permitting said polymer foam impression to solidify while in corrective pressure contact with said region of the spine to be treated, without restrictively enveloping any portion of the body;
    (h) freely removing said portion of said spine to be treated from the confines of said impression after a period of from approximately fifteen to forty-five minutes; and
    (i) freely repositioning said region of the spine to be treated on said containment reinforced impression for a period of from five to forty-five minutes daily to correct any dysfunction which may have occurred since the previous use of said reinforced impression.

2. The method of claim 1, including the step of encasing said containment means in a pliable membrane baglike means having an open end and using said open end for access to said containment means for placing said polymer foam therein.

* * * * *